(12) United States Patent
Stanziola et al.

(10) Patent No.: US 12,019,156 B2
(45) Date of Patent: Jun. 25, 2024

(54) ACOUSTIC SUB-APERTURE PROCESSING FOR ULTRASOUND IMAGING

(71) Applicant: IMPERIAL COLLEGE INNOVATIONS LIMITED, London (GB)

(72) Inventors: Antonio Stanziola, London (GB); Mengxing Tang, London (GB)

(73) Assignee: IMPERIAL COLLEGE INNOVATIONS LIMITED, London (GB)

( * ) Notice: Subject to any disclaimer, the term of this patent is extended or adjusted under 35 U.S.C. 154(b) by 195 days.

(21) Appl. No.: 16/310,181

(22) PCT Filed: Jun. 16, 2017

(86) PCT No.: PCT/GB2017/051766
§ 371 (c)(1),
(2) Date: Dec. 14, 2018

(87) PCT Pub. No.: WO2017/216578
PCT Pub. Date: Dec. 21, 2017

(65) Prior Publication Data
US 2019/0196013 A1 Jun. 27, 2019

(30) Foreign Application Priority Data
Jun. 16, 2016 (GB) .................................... 1610504

(51) Int. Cl.
*G01S 15/89* (2006.01)
*A61B 8/06* (2006.01)
(Continued)

(52) U.S. Cl.
CPC ............ *G01S 15/8927* (2013.01); *A61B 8/06* (2013.01); *A61B 8/488* (2013.01);
(Continued)

(58) Field of Classification Search
CPC ............ G01S 15/8927; G01S 15/8915; G01S 15/8977; G01S 15/8979; G01S 7/52046;
(Continued)

(56) References Cited

U.S. PATENT DOCUMENTS

| 5,423,318 A | 6/1995 | Li et al. |
| 5,544,128 A * | 8/1996 | Kim .................... G01S 7/52095 367/103 |

(Continued)

FOREIGN PATENT DOCUMENTS

WO WO-2015/147471 A1 10/2015

OTHER PUBLICATIONS

Holfort, I. K., Austeng, A., Synnevåg, J. F., Holm, S., Gran, F., & Jensen, J. A. (Sep. 2009). Adaptive receive and transmit apodization for synthetic aperture ultrasound imaging. In 2009 IEEE International Ultrasonics Symposium (pp. 1-4). IEEE. (Year: 2009).*

(Continued)

*Primary Examiner* — Jason M Ip
*Assistant Examiner* — Renee C Langhals
(74) *Attorney, Agent, or Firm* — MARSHALL, GERSTEIN & BORUN LLP

(57) ABSTRACT

A method for ultrasound data processing includes transmitting an ultrasound excitation signal from each element of a transducer array and receiving a response signal from each element of a transducer array. Each response signal corresponds to a respective channel. Each response signal is sampled at one or more time points in the response signal to create a plurality of samples, each sample corresponding to a channel and a time point. The samples are divided into at least two groups. Response signals from the first group are beamformed and response signals from the second group are beamformed separately. The process is repeated over multiple data frames. The beamformed signals of each group are (Continued)

correlated over the multiple data frames and beamformed signals having a lower degree of correlation or negative correlation are selectively attenuated. An image output is generated from the correlation output.

17 Claims, 9 Drawing Sheets

(51) Int. Cl.
  *A61B 8/08* (2006.01)
  *G01S 7/52* (2006.01)
  *G10K 11/34* (2006.01)

(52) U.S. Cl.
  CPC ...... *G01S 7/52046* (2013.01); *G01S 15/8915* (2013.01); *G01S 15/8977* (2013.01); *G01S 15/8979* (2013.01); *G10K 11/341* (2013.01); *G10K 11/346* (2013.01); *G01S 7/52039* (2013.01)

(58) Field of Classification Search
  CPC .............. G01S 7/52039; G10K 11/341; G10K 11/346; A61B 8/52; A61B 8/06; A61B 8/488
  USPC .......................................................... 600/459
  See application file for complete search history.

(56) References Cited

U.S. PATENT DOCUMENTS

| | | | |
|---|---|---|---|
| 5,570,691 A | 11/1996 | Wright et al. | |
| 5,676,148 A * | 10/1997 | Koo | G01S 15/584 600/447 |
| 7,399,279 B2 * | 7/2008 | Abend | A61B 8/06 600/450 |
| 2003/0149362 A1 | 8/2003 | Azuma et al. | |
| 2009/0112092 A1 | 4/2009 | Bae et al. | |
| 2009/0141957 A1 * | 6/2009 | Yen | G01S 15/8977 382/131 |
| 2009/0204003 A1 * | 8/2009 | Guracar | A61B 8/06 600/458 |
| 2015/0374341 A1 | 12/2015 | Chen et al. | |
| 2018/0161011 A1 * | 6/2018 | Owen | G01S 7/52022 |
| 2020/0138401 A1 * | 5/2020 | Haugaard | G01S 15/8984 |

OTHER PUBLICATIONS

International Search Report issued in PCT Patent Application No. PCT/GB2017/051766 dated Sep. 19, 2017.
Written Opinion issued in PCT Patent Application No. PCT/GB2017/051766 dated Sep. 19, 2017.
Combined Search and Examination Report issued in Great Britain Patent Application No. 1610504.1 dated Aug. 24, 2016.
Holfort et al., "Adaptive Receive and Transmit Apodization for Synthetic Aperture Ultrasound Imaging," *Ultrasonics Symposium*, (2009).
David Cosgrove, "Ultrasound contrast agents: An overview", European Journal of Radiology. 60:324-330 (2006).
Stanziola et al., "Ultrasound Imaging with Microbubbles", IEEE Signal Processing Magazine, 111-117 (2016).
Simpson et al., "Pulse Inversion Doppler: A New Method for Detecting Nonlinear Echoes from Microbubble Contrast Agents", IEEE Transactions on Ultrasonics, Ferroelectrics, and Frequency Control, 46:372-382 (1999).
Yildiz et al., "Correction of Non-Linear Propagation Artifact in Contrast-Enhanced Ultrasound Imaging of Carotid Arteries: Methods and In Vitro Evaluation", Ultrasound in Med. & Biol., vol. 41, No. 7: 1938-1947 (2015).

Lin et al., "Ultrasound Contrast Imaging: Influence of Scatterer Motion in Multi-Pulse Techniques", IEEE Transactions on Ultrasonics, Ferroelectrics, and Frequency Control, vol. 60 No. 10: 2065-2078 (2013).
L.S. Wilson, "Description of Broad-Band Pulsed Doppler Ultrasound Processing using the Two-Dimensional Fourier Transform", Ultrasonic Imaging, 13:301-315 (1991).
Montaldo et al., "Coherent Plane-Wave Compounding for Very High Frame Rate Ultrasonography and Transient Elastography", IEEE Transactions on Ultrasonics, Ferroelectrics, and Frequency Control, vol. 56 No. 3: 489-506 (2009).
Mace et al., "Functional Ultrasound Imaging of the Brain: Theory and Basic Principles", IEEE Transactions on Ultrasonics, Ferroelectrics, and Frequency Control, vol. 60 No. 3: 492-506 (2013).
Bercoff et al., "Ultrafast Compound Doppler Imaging: Providing Full Blood Flow Characterization", IEEE Transactions on Ultrasonics, Ferroelectrics, and Frequency Control, vol. 58, No. 1: 134-147 (2011).
Errico et al., "Transcranial functional ultrasound imaging of the brain using microbubble-enhanced ultrasensitive Doppler", NeuroImage, 124:752-761 (2016).
Osmanski et al., "Ultrafast Doppler Imaging of Blood Flow Dynamics in the Myocardium", IEEE Transactions on Medical Imaging, vol. 31 No.8: 1661-1668 (2012).
Demené et al., "Spatiotemporal Clutter Filtering of Ultrafast Ultrasound Data Highly Increases Doppler and fUltrasound Sensitivity", PubMed, 34. 10.1109/TMI.2015.2428634 (2015).
Li et al., "Small-diameter Vasculature Detection with Coherent Flow Power Doppler Imaging", IEEE International Ultrasonics Symposium Proceedings, 1-4 (2015).
Lediju et al., "Short-Lag Spatial Coherence Imaging", IEEE International Ultrasonics Symposium Proceedings, 987-990 (2010).
Lediju et al., "Short-Lag Spatial Coherence of Backscattered Echoes: Imaging Characteristics", IEEE Transactions on Ultrasonics, Ferroelectrics, and Frequency Control, vol. 58 No. 7: 1377-1388 (2011).
Bullitt et al., "Vessel Tortuosity and Brain Tumor Malignancy: A Blind Study", Academic Radiology, vol. 12 No. 10: 1232-1240 (2005).
Peter Carmeliet, "Angiogenesis in health and disease", Nature Medicine, vol. 9 No. 6: 653-660 (2003).
Gessner et al., "Acoustic Angiography: A New Imaging Modality for Assessing Microvasculature Architecture", International Journal of Biomedical Imaging, vol. 2013 Article ID 936593: 1-9 (2013).
Demené et al., "Ultrafast Doppler reveals the mapping of cerebral vascular resistivity in neonates", Journal of Cerebral Blood Flow & Metabolism, 34: 1009-1017 (2014).
Macé et al., "Functional ultrasound imaging of the brain", Nature Methods, vol. 8 No. 8: 662-666 (2011).
Zion et al., "Super-Resolution Ultrasound Imaging of Vascular Structures with High Temporal Resolution", No. arXiv: 1601.05710. 2016, 1-11 (2016).
Seo et al., "Sidelobe Suppression in Ultrasound Imaging Using Dual Apodization with Cross-Correlation", IEEE Transactions on Ultrasonics, Ferroelectrics, and Frequency Control, vol. 55 No. 10: 2198-2210 (2008).
Shin et al., "Robust Ultrasonic Reverberation Clutter Suppression Using Multi-Apodization with Cross-correlation", IEEE International Ultrasonics Symposium Proceedings, 543-546 (2014).
Leow et al., "Flow Velocity Mapping Using Contrast Enhanced High-Frame-Rate Plane Wave Ultrasound and Image Tracking: Methods and Initial In Vitro and In Vivo Evaluation", Ultrasound in Med. & Biol., vol. 41 No. 11: 2913-2925 (2015).
Synnevåg et al., "Minimum variance adaptive beamforming applied to medical ultrasound imaging", IEEE Ultrasonics Symposium, 1199-1202 (2005).
Office Action issued in European Patent Application No. 17740065.2 dated Aug. 23, 2021.

* cited by examiner

ACOUSTIC SUB-APERTURE PROCESSING FOR ULTRASOUND IMAGING

TECHNOLOGICAL FIELD

The present invention relates to ultrasound imaging techniques, and in particular to techniques for processing received acoustic data from an ultrasound transducer array in order to improve image quality.

BACKGROUND

Ultrasound imaging of vascular flow can be done without or with contrast agents. Blood cells can generate weak but often detectable echoes. The aim of contrast-enhanced ultrasound imaging is to use the high echogenicity of micrometer-sized bubbles to improve the backscattered signal from blood vessels, in order to obtain vascular information from regions that would otherwise be masked by the much stronger echoes from surrounding tissues [1].

More than simply enhancing the signal from vessels, microbubbles also exhibit a non-linear response which can be exploited to differentiate them from the linear echoes of surrounding structures, by using appropriate transmission/reception techniques [2]. The vast majority of such methods assume time invariance of the bubble response over a few transmissions, by combining multiple acquisitions with different settings to attenuate tissue echoes and enhance contrast signal. One of the simplest and most widely employed methods for doing so is Pulse Inversion (PI) [3], where two opposite pulses are sent in two different transmissions and then the received signals are summed together, to suppress fundamental (tissue) and odd harmonics, and keeping even harmonics which are assumed to generate only from microbubbles.

Some of the assumptions of such approaches, however, are found to be invalid for many scanning conditions. For example, non-linear wave propagation and its passage through microbubble clouds [4] both generate harmonics that are reflected by linear structures and therefore falsely appear as contrast signal in the final image. Also, even very small motions of the tissue can cause a misalignment of the received echoes, so as to increase the response of tissue and reducing the response of microbubbles [5].

Various ways exist to deal with such issues. If tissue motion is null or negligible, one can assume that the signal coming from tissue (regardless of its frequency content) at a definite spatial location is slowly varying in consecutive transmissions, in contrast to microbubble and/or blood signal which varies both because the microbubbles and/or blood scatterers are dragged by the blood flow and because the microbubble response can vary between successive pulses. This means that by filtering (e.g. with a wall filter) a stack of acquired frames, over slow time, it is possible to enhance the signal coming from time-varying sources such as microbubbles or blood cells. This is the principle behind all Doppler techniques, with and without contrast agents [3].

SUMMARY OF THE DISCLOSURE

In this disclosure, a new technique is described and compared with Power Doppler estimation, i.e. the power of a Doppler signal. The technique is applicable to imaging with and without contrast agents, and may be generally applicable to all ultrasound acquisition methods and targets, e.g. any type of ultrasound transmission (focused, unfocused, synthetic aperture). In this document, imaging with high frame-rate ultrasound and microbubble contrast agents is given as an illustrative example.

The quality of Doppler signal estimation depends on the number of samples, that is the number of transmissions or acquisitions/frames used to estimate the echo at a given location, and the sampling rate, which is the time between successive transmissions. In classical focused line-by-line scanning, a trade off must be made between the field of view and the number of samples used because of the time required to acquire all the necessary lines. Using ultrafast acquisition with non-focused waves, the number of samples available is not any more limited by field of view [7].

Imaging based on such ultrafast acquisition has been shown to have, for the same frame rate, a significantly expanded field of view compared to classical focused approaches [8] and a wide range of applications. For example, besides classical Colour and Power Doppler applications it has been used to characterize blood flow in small vessels [9], to create maps of brain areas activation with a better spatiotemporal resolution than fMRI via transcranial acquisition in mice or to characterize the blood flow dynamics in the myocardium [11].

However, even with contrast agents, ultrafast acquisition, and existing signal processing methods such as Singular Value Decomposition (SVD), the signal strength from within blood is still dependent on ultrasound frequency and depth and for small vessels the signal can still be weak relative to background tissue and/or noise. However, SVD assumes that noise has a uniform variance across the field of view, which is an invalid assumption in the context of ultrasound imaging because of the depth-dependent amplification from time gain compensation (TGC). This results in the presence of noise in the final image, which in standard implementations increases with depth.

There have been several studies aimed at improving the quality of Power Doppler images via different type of processing, e.g. including the spatial dimension or by employing statistical analysis. For example, the joint use of spatial and temporal information can be found in [12], where the authors propose a Singular Value Decomposition of an ultrasound video sequence and then use only the central singular values to reconstruct the video, as they are supposed to be generated by flowing contrast agent only. This has shown very promising results, but exhibits a high computational demand which makes real time implementation difficult.

Recently, Li et al. have presented a method based on short-lag spatial coherence imaging which is able to improve the sensitivity of Power Doppler imaging. Their processing, for each pixel, evaluates the coherence of the received echo by computing the zero-lag cross correlation of signals from different channels over a small kernel around the point of interest, in the depth dimension. The authors show very good improvements in SNR, up to 30 dB in experimental conditions, showing that cross-correlation can be used as an effective method for reducing clutter and electronic noise. Unfortunately, evaluating the normalized cross-correlation for a big number of channel pairs is computationally expensive, and a robust spatial cross correlation estimation can cause blurring in the axial direction due to the kernel size [15]. Moreover, the modified Loupas estimator used limits the SNR improvement to the chosen kernel size, because of the incoherent summation over different frames.

It is an object of the present invention to provide an improvement in processing methods for received data from an ultrasound machine, in order to enable the generation of higher quality images, preferably in real time. The techniques may particularly improve imaging of, for example, human or animal vasculature. The methods may be particularly suitable for ultrasound apparatus generating large amounts of data from ultrafast acquisitions. The processing methods may assist in reducing computational complexity and/or keeping the computational complexity as low as possible in order to facilitate real-time implementation of the processing methods and therefore enhancing their applicability to real clinical settings.

According to one aspect, the present invention provides a method for ultrasound data processing comprising:
i) transmitting ultrasound excitation signals from elements of a transducer array;
ii) receiving response signals from elements of the transducer array, each response signal corresponding to a respective channel;
iii) sampling each response signal at one or more time points in the response signal to create a plurality of samples, each sample corresponding to a channel and a time point;
iv) dividing the samples into at least two groups;
v) beamforming the response signals from the first group;
vi) beamforming the response signals from the second group;
vii) repeating steps i) to vi) for M data frames, where M is greater than 1;
viii) correlating the beamformed signals of each group and generating an image output therefrom.

Correlating the beamformed signals of each group may comprise using any of a correlation function, a coherence function or a covariance function. Step viii) may comprise calculating a covariance matrix R between channels over the M data frames, and generating the image output therefrom, and may further include averaging with weights all or some of the elements of the covariance matrix.

The transducer array used for transmitting the excitation signals may be the same transducer array used for receiving response signals. The expression 'transducer array' is intended to encompass (i) an array of elements where the elements may all be on the same substrate or transducer head and (ii) an array of elements where the elements may be distributed across multiple substrates or transducer heads, and (iii) a transducer array comprising selected elements of a larger array where only selected elements of the larger array are used for each transmit and/or receive operation. In an example, an ultrasound signal is transmitted from each element of the array and a response signal is received from each element of the, or a different, array. In another example, transmission of the excitation signals may be from selected ones of the elements in the array for a first group and from a different selection of ones of the elements for the second group, and receiving the response signals may be from all the elements of the array. The first group may comprise samples from the same time point of each of a plurality of channels and the second group may comprise samples from that same time point of each of a different plurality of channels. The first group may comprise samples from a first time point of each of a plurality of channels and the second group may comprise samples from a second time point of each of the same plurality of channels. The first group may comprise samples from a first time point of each of a first plurality of channels and a second time point of each of a second plurality of channels, and the second group may comprise samples from the first time point of each of the second plurality of channels and the second time point of each of the first plurality of channels. The at least two groups of samples may be selected according to at least one of the following conditions: each sample is allocated to only one group; each group has the same number of samples; a majority of adjacent elements in the array are allocated to different groups, a majority of the data samples are not common in the different groups, samples are allocated to the groups randomly or adaptively depending on the received data, e.g. by optimizing a measure of the received data. An example of adaptive allocation could be to choose the apertures in order to minimize the total correlation amplitude.

Step viii) of the method may comprise correlating the beamformed signals of each group over the M data frames. Step viii) of the method may further include selectively attenuating beamformed signals having a lower degree of correlation or a negative or inverse correlation. The beamforming of step v) may comprise, for a pixel of an image space, summing the set of samples of the first group, and the beamforming of step vi) may comprise, for said pixel of the image space, summing the set of samples of the second group.

The method may further include filtering each beamformed set of response signals to suppress clutter signal components, or other unwanted components. Possible unwanted components are, for example, targets moving in a certain velocity range. Filtering each beamformed set of response signals may comprise filtering with a high pass filter. Such filtering can be performed either with a classical high pass filter applied pixel-wise, or with a more complex filtering technique such as SVD. The high pass filter may be one of a derivative estimator; an FIR filter, a second order FIR filter and an IIR filter, for example.

Step viii) of the method may comprise performing a cross-correlation of the beamformed signals of at least the first and second groups. Step viii) may comprise attenuating the correlation signal as a function of the phase value. Step viii) may comprise applying different filters for each aperture so as to include the phase of the Doppler spectrum in the final correlation value, or using phase components of the correlation signal, to infer blood dynamics information. The blood dynamics information may comprise direction of flow.

The method may further include normalizing the cross-correlation values with respect to the norm of the beamformed response signals. Step viii) of the method may comprise using different filters for each group, in order to obtain a more complex filtering to select different flow velocities. Step viii) of the method may comprise include phase information in the correlation to select different flow velocities. The different filters may be designed with a phase shift between positive and negative frequencies, in order to extract flow direction information.

The method may further include displaying a magnitude of the correlation signals for each of a plurality of pixels in a two dimensional array of pixels of image space, in a process of ultrasound imaging. The process may be carried out substantially in real time with the collection of response signals in respect of each of a plurality of pixels of image space and for a succession of data frames. The samples may be allocated different groups for successive data frames.

According to another aspect, the invention provides an ultrasound processing apparatus configured to carry out the process of any of the methods described above. According to another aspect, the invention provides a computer program product, comprising a computer readable medium having thereon computer program code means adapted, when said program is loaded onto a computer, to make the computer execute the procedure of any of the methods defined above. According to another aspect, the invention provides a computer program, distributable by electronic data transmission, comprising computer program code means adapted, when said program is loaded onto a computer, to make the computer execute the procedure of any of the methods defined above.

According to another aspect, the present invention provides an ultrasound imaging apparatus comprising:
a transducer array comprising a plurality of transducer elements, the transducer array configured to generate response signals from elements of the array, in response to ultrasound excitation, each response signal corresponding to a respective channel;
a sampling module configured to sample each response signal at one or more time points in the response signal to create a plurality of samples, each sample corresponding to a channel and a time point;
a first beamforming module configured to beamform the response signals from a first group of the channels;
a second beamforming module configured to beamform the response signals from a second group of the channels;
the first and second beamforming modules configured to repeat the beamforming for each respective group for M data frames, where M is greater than 1;
a correlation module configured to correlate the beamformed signals of each group and generate an image output therefrom.

The correlation module may be configured to correlate the beamformed signals of each group using any of a correlation function, a coherence function or a covariance function. The correlation module may be configured to calculate a covariance matrix R between channels over the M data frames, and may be further configured to average with weights all or some of its elements.

BRIEF DESCRIPTION OF THE DRAWINGS

Embodiments of the present invention will now be described by way of example and with reference to the accompanying drawings in which:

FIG. 9 shows in vivo results for image processing on the same rabbit kidney as in FIG. 6, in which FIG. 9(a) shows flow information at a specific flow velocity range, FIG. 9(b) shows a flow direction coded vascular image, and FIG. 9(c) shows an enlarged and enhanced version of FIG. 9(b);

DETAILED DESCRIPTION

Figure 1:
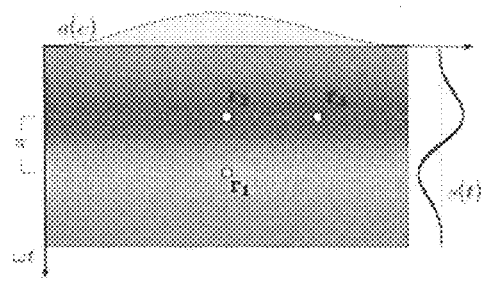
FIG. 1 shows a graph of the RF field in grayscale shown against time (vertical axis) and channel (horizontal axis) indicating sample locations $r_1$ and $r_2$ recorded by the same channel with half-wavelength separation and sample locations $r_2$ and $r_3$ recorded by different channels but with the same phase.

The method described herein is referred to as Acoustic Sub-Aperture Processing (ASAP), and may be used for a number of purposes including the following examples:
1) generation of real time high quality images, particularly though not exclusively of the vasculature morphology, also known as angiographic maps;
2) generation of real time blood dynamics information, such as in e.g. Doppler studies.

Angiographic maps are very useful in clinical practice, as vessel morphology is a very good indicator of diseases, such as cancer and many others [17]. Also some other researchers have realized angiographic maps using ultrasound, for example in a custom built transducer has been realized for such a purpose.

Blood flow images, on the other hand, are one of the main reasons for which ultrasound is used for vascular imaging and there are a lot of studies and clinical applications in such direction [19], with and without contrast agent. As already mentioned, one of the most used techniques for such a task is Power Doppler, which provides a sensitive method for characterizing blood flow [20], [21], [22].

The major limitation of Power Doppler is the lack of ability to distinguish between Doppler and noise power, and therefore the signal-to-noise ratio after beamforming and compounding dictates the minimum signal which can be meaningfully distinguished from noise. The acoustic sub-aperture processing (ASAP) techniques described herein, however, use decorrelation of noise between acquisitions and channels in order to remove noise power from the estimation and return a true Doppler signal. In this sense, ASAP largely outperforms Power Doppler as it can theoretically achieve infinite SNR regardless of the quality of each scan, a useful property when the signal to estimate is close to or at the noise floor [23].

A. Beamforming

The sound emitted from a scatter or microbubble s(t), after excitation with an ultrasound pulse can be approximated by an oscillation at a certain frequency to multiplied by a Gaussian window η(t)

$$q(t) = \eta(t) S_0 e^{j2\pi(2f_0)t + \phi} \tag{1}$$

With dynamical receive beamforming, we try to estimate the sound coming from a specific location, which is represented as a pixel value. If contrast agents are employed, such sound is emitted by microbubbles, after ultrasound excitation. Pulse inversion can be used to enhance the power of signals emitted by microbubbles compared to tissue. From now on, we refer the measured data to be from a single pulse transmission and reception, although all the proposed analysis applies to Pulse Inversion and other sequences too. If the image area covered by the pixel is small enough compared to the scattered wavelength, we can consider all the scatterers (microbubbles or blood scatterers) in that pixel to be in the same position and therefore define the signal emitted at the pixel region as $$s(t, n) = \sum_i q_i(t, n) \tag{2}$$

where n∈Z is the slow time, which is used to denote that the signal changes for successive frames as different scatterers flow in the region covered by the pixel, and q is the signal emitted from a single scatterer.

This signal is recorded by the N, channels of the transducer array, forming the signals $$\overline{b}_i(t,n) = a_i(s(t+\tau_i,n) + c(t+\tau_i,n)) + e_i(t,n), \tag{3}$$

where $a_i$ is the attenuation of the wave from the source to the channel, $\tau_i$ is the two way propagation time, c(t, n) is the unwanted clutter signal (coming from non-linear propagation and small motions), e is noise and i∈{1, ..., $N_c$}. Note that the noise is made of two components: the electronic noise, which is usually considered as a zero mean Gaussian random variable, and the interference from off-axis targets, which has zero mean and unknown second order statistics (i.e. we don't know how the interference pattern is correlated between different channels and different times). The noise also includes artefacts coming from second harmonic propagation given by dispersion, which in the slow time have non-zero mean and are highly correlated. In order to extract the envelope information from the received acoustic signals, the Hilbert transform is used to generate the complex analytical signal of the received data for each channel: this means that all the signals we are going to deal with, from now on, are complex.

This stage exemplifies steps of i) transmitting an ultrasound excitation signal from each/some element of a transducer array; and ii) receiving a response signal from each/some element of a transducer array, each response signal corresponding to a respective channel. The excitation signal can be any suitable excitation pulse or pulse sequence, such as single pulse, pulse inversion, chirp, amplitude modulated pulse or frequency modulated pulse.

The emitted response signal may be recovered in several ways. Here we will describe the so-called Delay and Sum technique, but the technique described doesn't rely on a particular type of beamforming method. Recovery from $\overline{b}_i$ can be done by delaying the waveform of each channel by the proper amount of time $\tau_i$ and then by summing them together. This dynamic beamforming is called Delay and Sum (DAS), and can be described mathematically as (dropping the slow time n for simplicity):

$$p = \sum_{i=1}^{N_c} w_i \overline{b}_i(\tau_i) = \sum_{i=1}^{N_c} w_i b_i = w^T b \tag{4}$$

where b=($b_1$, ..., $b_{N_c}$) is the steered vector containing all the delayed measurements from all the channels, w is the vector of apodization weights which in all the experiments will be a Hanning window with variance proportional to the depth, so to compensate for the directional sensitivity of each channel.

When using the Delay and Sum (DAS) method to beamform a specific location p, what we are doing in the RF domain by the delay operation is to wrap the receive data such that a wave emitted from p is plane with zero angle with respect to the channels c, and centred in zero. This is shown in FIG. 1: the RF field is the grayscale image shown against time and channels. The function a(c)≥0 represents the amplitude weighting function that takes into account wave propagation and channel sensitivity, and is multiplied to each channel signal. In reality we have only sample of this field, and we can estimate others using interpolation.

Looking at a sample in the location $r_1$ and $r_2$, for example, they are recorded by the same channel and therefore multiplied by the same weight. More importantly, they are spaced by half a wavelength and therefore their complex values have a phase shift (or rotation) by a factor of π. On the other hand, the values at $r_2$ and $r_3$ have the same phase but are multiplied by different weights because they are recorded by different channels. As the phase value only depends on the frequency of the received echo, ω=2$f_0$, we have knowledge of such phase shift simply because we know the transmitted frequency, except for a bias of φ which is the same everywhere.

This means that we can coherently sum different values of the same channel, spaced by a time interval Δt, by rotating the RF data by a phase of θ=ωΔt.

In DAS, after delaying, only the values of the RF data at time zero are summed together. This can be seen as sampling the RF field at each channel location, at the same time instant t=0. These samples are shown in FIG. 2A(a) as white dots, and we see that they are all aligned on the same time point therefore no phase shifting is needed to coherently sum them.

B. ASAP Processing

In the proposed ASAP processing scheme, the channel waveforms are still delayed as discussed above, but the RF data sampled by different channels and/or different time points of the waveforms are then split into at least two groups, each comprising multiple samples. The groups preferably each comprise the same number of samples. Samples can be taken either at t=0, as in the DAS scheme above, or at different time points of the waveform, in which case the values are first phase shifted to coherently sum them. Alternatively, it is possible to split the transducer during the transmission phase and then receive from the entire transducer aperture: in this way, the groups are given by the different acquisitions, each one with a different transmit aperture.

Figure 2A:
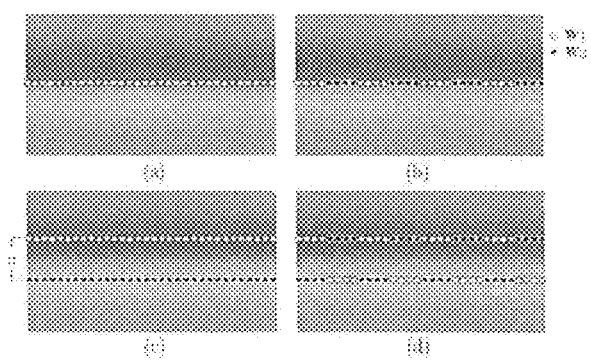
FIG. 2A shows a graph of the RF field in greyscale shown against time and channel, indicating different possible channel and/or time point groupings.

For example, in FIG. 2A(b) two groups are formed by using four samples for each group, alternatingly, which is equivalent to splitting the channels into two groups. In FIG.

Figure 2B:
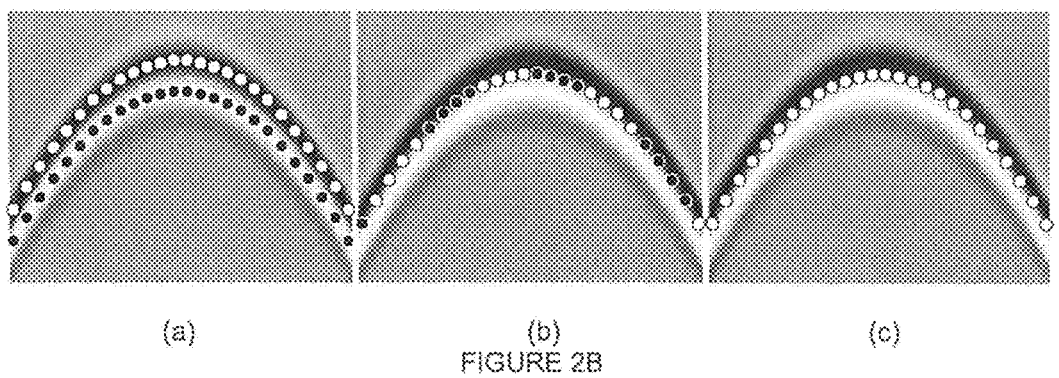
FIG. 2B shows an alternative representation to that shown in FIG. 2A of different ways of grouping RF measurements for cross correlation processing where the black and white dots represent different groups and the single group configuration of FIG. 2B(c) corresponds to standard delay and sum beamforming.

2A(c) on the other hand, one group is formed by taking all the channel samples at t =0 and the other group is formed by taking the samples with a lag (e.g. in this example, half a wavelength): note that this can be seen as a very simple matched filter, therefore it performs compression of the received wave, improving the axial resolution. FIG. 2(*d*) is a mixture of the two approaches. FIG. 2B shows illustrations similar to FIGS. 2A(c), 2A(b) and 2A(a) schematically illustrating corresponding equal time points, but without taking into account delays introduced by delay and sum when targeting specific spatial locations. The figures of FIG. 2B therefore represent the raw data acquired by each channel.

Thus, in a general aspect, each response signal from an element in the transducer array is sampled at one or more time points in the response signal waveform, to create a plurality of samples where each sample corresponds to a particular channel and a particular time point in that channel response signal.

How to select the samples for each group is discussed later. In a general aspect, the received signals are divided into at least two groups and the response signals are beamformed separately for each group, e.g. beamforming the response signals from the first group; and beamforming the response signals from the second group, and so on for each group where there are more than two.

In one arrangement, a first group may contain samples from the same time point of each of a plurality of channels and a second group may comprise samples from that same time point of each a different plurality of channels. This is exemplified in FIG. 2A(b) and, at least in part, in FIG. 2A(d), as illustrated by the black and white dots.

In another arrangement, a first group may comprise samples from a first time point of each of a plurality of channels and a second group may comprise samples from a second time point of each of the same plurality of channels. This is exemplified in FIG. 2A(c) and, at least in part, in FIG. 2A(d).

In another arrangement, a first group may comprise samples from a first time point of each of a first plurality of channels and a second time point of each of a second plurality of channels, and the second group may comprise samples from the first time point of each of the second plurality of channels and the second time point of each of the first plurality of channels. This is exemplified in FIG. 2A(d).

As this method may only remove uncorrelated noise sources between different groups, it may be preferable to take into account the nature of noise when grouping the samples. For example, if each element of the imaging probe (transducer array) is known to be electronically independent of the others, then we can assume that the noise generated by the electronics is uncorrelated between channels and therefore the architecture of the system doesn't impose any constraint upon the choice of grouping. On the other hand, if some channels share a common electronic pathway in the system, it is possible that the electronic noise they carry is indeed correlated between different elements and therefore samples coming from such channels should not be grouped together. Note, however, that we may take into account cross-correlation at lag zero, and therefore if there is a correlation at a certain lag different than zero, we have no constraints again on our design.

Interference noise, caused by off-axis targets, may be correlated between channels and in the image this translates as the undesired correlation between side-lobes of different spatial locations. A simple method to deal with this is to design the grouping such that the side lobes have a negative correlation value, so that we can distinguish them from main lobe signals which have a positive correlation, as described later in see Section C. Another way is to use multiple apertures/groups, in which case we are reducing the correlation of side lobes by averaging the different correlation values given by different pairs of apertures/groups, again as described in Section C. Note that averaging the correlation of different group pairs corresponds to the (possibly weighted) average different elements of the channel covariance matrix R. This means that another possible approach to implement the method would be to first calculate the covariance matrix R between channels over frames, and then average with weights all or some of its element, although such implementation would increase computational burden.

Finally, it is also possible to have some channels in common between two different groups: this is both because it may help in reducing interference noise, and because ASAP output is not much degraded if there are a few channels in common.

Furthermore, we can dynamically change the sample grouping for each frame acquisition, e.g. in software/GPU/FPGA based beamforming, as another possible way to reduce the above interference noise. One way to use this to reduce the interference noise would be to randomly change the way we group at each acquisition/frame. In this way, although the correlation of the main-lobe will always be real and positive, the correlation of side-lobes will have a random phase value at each frame. Averaging them over the M frames will therefore reduce the power of side lobes compared to main lobe, so to reduce the interference noise. Another way to reduce the influence of interference targets, for example, would be to calculate the two groups such as to minimize the variance as done in Capon beamforming methods [28].

In a preferred arrangement, each group is beamformed by summing its samples. This can be seen as dynamically beamforming the same pixel at least twice with two orthogonal apodizations:

$$p_1=w_1^T b, \; p_2=w_2^T b \qquad (5)$$

with $w_1^T w^2=0$, where b contains all the samples, already phase shifted if necessary, and p, is the pixel value after beamforming for the aperture i. If the channels are divided into more than two groups, each group is beamformed by summing its respective elements such that the same pixel is beamformed a number of times according to the number of groups. Different processes for beamforming, i.e. other than the summation described above, may be used.

In the examples discussed herein, we only investigate images given by apodizing the elements using depth-varying Hanning windows, for which the orthogonality may be enforced by using each element only for one of the two images, across the whole aperture. Preferably, we split the samples into two groups. There are other ways of choosing the apodizations, discussed later. Splitting the channels in two groups avoids substantially increasing the computational complexity of the DAS beamformer, as discussed below.

For a large enough number of channels in each group, by the central limit theorem we expect that the noise is Gaussian distributed, and therefore by averaging several acquisitions we should be able to increase the SNR. The expected values (over a large number of channels) of the pixels $p_1$ and $p_2$ are therefore:

$$\mu_{p_i} = E[p_i] = E[w_i^T b] = E[w_i^T((s+c)a+e))] \quad (6)$$

$$= E\left[\frac{N_c}{2}k_i(s+c) + w_i^T e\right] = \frac{N_c}{2}k_i(s+c) + E[w_i^T e]$$

$$= \frac{N_c}{2}k_i(s+c)$$

where in the second row we have defined $k_i = w_i^T a$, and in the third row we have used the fact that the expected value of our noise is zero. In reality, the estimation will be done over a finite number of samples, so the actual measured value will be $$\mu_{p_i}^- = \frac{N_c}{2}k_i(s+c) + e_i, \quad (7)$$

where $e_i$ is to account for the noise of averaging over a finite number of channels.

This shows that we are estimating the signal: note that, so far, the contrast and clutter signal are not distinguished. To do that, as for Power Doppler, a wall filter may be used. For fast computation, a simple FIR filter may be used, which is the backward finite difference filter with impulse response $h = (½)[1, -1]$: that is, we are simply subtracting consecutive frames. This is probably the simplest high pass filter, and being a FIR filter it doesn't require any initialization.

Other filters may be used to suppress the clutter signal: this is analogous to what is done in Colour or Power Doppler analysis, with the difference that while without contrast agent the signal s is much weaker than c, here the opposite is true, therefore one can use a much simpler filter which is more suitable for real time processing. Any wall filter (even adaptive) can be used. Four examples are given in the table below.

| Filter |
| --- |
| $F_1(z) = \frac{1}{2}(1 - z^{-1})$ |
| $F_2(z) = -0.37 - 0.48z^{-1} + 0.85z^{-2}$ |
| $F_3(z) = \dfrac{1 - 2z^{-1} + z^{-2}}{1 - 1.66z^{-1} + 0.73z^{-2}}$ |
| $F_4(z) = \dfrac{4\xi - 8\xi z^{-1} + 4\xi z^{-2}}{(\omega_c^2 + 4)\xi + 2\omega_c + (2\omega_c^2 - 8)\xi z^{-1} + ((\omega_c^2 + 4)\xi - 2\omega_c)z^{-2}}$ |

The FIR filter $F_1(z)$ is just a simple derivative estimator and is the simplest of all, as it can be realized just by a subtraction of consecutive samples. $F_2(z)$ and $F_3(z)$ are respectively second order FIR and IIR filters, having the same normalized cutoff frequency of $0.1\pi$ rad/sample. The first one may be constructed using the Equiripple method and the second one may be a Chebyshev Type 1 high pass filter.

The last one, $F_4(z)$ is a discrete filter derived from a second-order high pass analog filter using the bilinear transform [15, 16], where $\omega = 2\pi f/f_T$ is the normalized frequency, $\omega_c$ is the cut-off frequency, $\eta$ is the damping ratio and $f_T$ is the frame-rate. The last design allows for the automatic adjustments of the wall filter coefficients for different scanning conditions (number of angles or depth), and for live adjustments of the cut-off frequency to cope with different patient motions. The derivation through bilinear transform from a stable filter also ensures the stability of the digital filter. The cut-off frequency may be set to 50 Hz, which for a frame acquisition rate of 1000 fps equals the cut off frequency of the other filters.

Thus, as exemplified above, in a general aspect each beamformed set of response signals from a respective group may be filtered with a high pass filter to suppress clutter signal components. In general, filtering is not essential in order to remove electronic noise, but it is preferable to compensate for clutter signals. If no relevant motion is present and contrast agent is employed, the method can be used in conjunction with low power transmissions (which minimize second harmonic generation) and microbubbles without any filtering at all.

The examples given are only an illustrative set of filters which are suitable for real time use. In general, the filtering method is a design choice which depends on the application and the user interests.

In the remaining part of the analysis, we assume that the clutter (static) signal has been removed, and the signal beamformed at each pixel is $$\overline{p}_i = w_i^T(sa + e), E[p_i] = \frac{N_c}{2}k_i s. \quad (8)$$

The remaining part of the process performs a cross correlation, in the slow time (i.e. from frame to frame, or over successive frames), of the obtained filtered beamformed signals of each group, $p_1[n]$ and $\overline{p}_2[n]$, where $\overline{x}$ denotes the complex conjugate of $x \in \mathbb{C}$, over a window of length M. In practice, M indicates the number of frames used in the estimation of the cross correlation value: the greater M, the better the estimation of the two images' cross correlation and therefore the quality of the image. On the other hand, the presence of large amplitude motion will cause blurring and artefacts for large M.

The reason behind performing this correlation step is to reveal how much the beamformed signals come from averaging of speckle noise, and how much comes from an actual target (i.e. a vessel). Intuitively, if the pixel belongs to the vessel, the signal recorded should come from contrast agent or blood scatterers, therefore it has to be correlated between the two apertures with a positive real correlation value. Conversely, if the measurements are mainly given by noise, the two values have no reason to show such a correlation, therefore we expect the cross correlation to be a complex number of any phase but relatively small magnitude. In fact, if the pixel belongs to a vessel, then we can assume that its signal $s[n]$ is much bigger than the noise after beamforming, given by $e[n]$ in eq. (7).

The correlation described above exemplifies a general step of correlating the beamformed signals of each group over M data frames. This may encompass cross-correlation or other correlation functions.

In reality, because speckle noise is not really Gaussian but it has a correlation length usually comparable to the sample distances, some care may be given in how the samples are split between the two groups, discussed below.

We approximate the cross correlation of two sequences $a[n]$ and $b[n]$ as follows:

$$c(a, b) = E[(a - \mu_a)\overline{(b - \mu_b)}] \simeq \sum_{n=0}^{M-1} (a[n] - \mu_a)\overline{(b[n] - \mu_b)}, \quad (9)$$

where the expected values are calculated over the slow time n and $\mu_x = E[x]$.

For our case, the mean value of both $p_1$ and $\overline{p_2}$ is zero, because of the high pass filtering, therefore we can simplify the calculation of the cross correlation $$c(p_1, p_2) = E[p_1 \overline{p_2}] = E[w_1^T(sa+e)\overline{(w_2^T(sa+e))}] \quad (10)$$

$$= E\left[\left(\sum_i w_i^1(a_i s + e)\right)\left(\sum_j \overline{w_j^2(a_j s + e)}\right)\right]$$

$$= E\left[\sum_i \sum_j w_i^1 \overline{w_j^2}(a_i s + e)\overline{(a_i s + e)}\right]$$

$$= \sum_i \sum_j w_i^1 \overline{w_j^2} E[(a_i s + e)\overline{(a_i s + e)}]$$

$$= w_1^T R_{p,p} w_2,$$

where $R_{p,p}$ is the cross correlation matrix between all channels' measurement over the slow time n.

Looking at the elements of matrix, we find $$R_{p,p}[i, j] = E[(a_i s + e_i)\overline{(a_j s + e_j)}] \quad (11)$$

$$= E[a_i \overline{a_j} \|s\|^2 + a_i s \overline{e_j} + \overline{a_j s} e_i + e_i \overline{e_j}]$$

$$= a_i \overline{a_j} E[\|s\|^2] + E[e_i \overline{e_j}]$$

with i,j channel indexes from 1 to $N_c$. Because both error and source signal have zero mean, we have that the first expected value is the power of s (over the slow time) $E[\|s\|^2] = \sigma_s^2$, and that $E[e_i \overline{e_j}] \cong \epsilon^2 \delta_{i,j}$ because we assume that different noise samples are uncorrelated. The value $\epsilon^2$ is the instantaneous noise variance and the symbol $\delta_{i,j}$ is the Kronecker delta.

Therefore the final cross correlation between the signal of the two apertures is $$c(p_1, p_2) = w_1^T R_{p,p} w_2 = w_1^T (A\sigma_s^2 + I\epsilon^2) w_2 \quad (12)$$

$$= w_1^T (A\sigma_s^2) w_2 + w_1^T (I\epsilon^2) w_2$$

$$= w_1^T A w_2 \sigma_s^2 = K\sigma_s^2,$$

where $A_{i,j} = a_i \overline{a_j} = a_i a_j$, as the $a_i$ are real, and in the last row we've used the fact that the two apodizations are made of different elements, therefore the diagonal elements of the diagonal matrix $I\epsilon^2$ are multiplied by zeros, so no contribution is given by the noise to the cross correlation.

In reality we will perform the cross correlation measure over a finite number of samples, therefore the noise will not completely cancel out and the matrix will not be exactly diagonal. The greater the number of frames used in the estimation, the better the noise cancellation. Note that this is fundamentally different than what happens in power Doppler, where the frame averaging improves the SNR spatial variance but not the actual SNR value which is fixed. Here we improve both.

The cross correlation between samples can therefore be realized by a simple multiplicative junction and averaging over M frames via a filtering operation with an FIR filter with impulse response $$H_{int}[z] = \sum_{k=0}^{M-1} z^{-k} \quad (13)$$

This is a windowing operation, therefore it may be advisable to have a different shape than a rectangle.

C. Sidelobes

The reasoning made so far requires the noise to be uncorrelated between channels. While this is true for electronic noise and potentially reverberations, it is not necessary a good model for clutter signal generated by the side- and grating-lobes from nearby vessels. In this case, instead of using the cross correlation between each channel pair as in [13], we can use the properties of alternating pattern apodizations [25], and split our groups by alternating the elements in each one, as done in FIG. 2(b). In this way, while the main lobe of each receive aperture will have the same phase, sidelobes will have opposite phase between the two apertures. This means that we can look at the phase of the cross correlation to distinguish between sidelobes, which will be close to t, contrary to a phase of 0 which is expected for the main lobe.

The work in [25] also shows that a rectangular apodization is advisable because of the smaller main lobe width, at the expense of bigger sidelobes. In this case, however, we may use a Hanning window across the apodization to avoid the negative cross correlation of sidelobes masking out the signal coming from a weaker nearby scatterer (i.e. a smaller vessel). That is, we may not take advantage of the higher resolution given by a rectangular apodization but in exchange we can gain a more reliable quantification of the power Doppler signal, which is the goal in many clinical applications. It should be noted, however, that the resolution is not made worse but just kept as good as for DAS beamforming with Hanning apodization (see Results section below).

It is also possible to use multiple apertures and cross correlate among them, where preferably each channel is used for only one group. In this case, the cross correlation can be calculated for every pair or some pairs of apertures which are non-overlapping or have little overlapping, and the average or weighted average cross correlation value returned. The use of multiple apertures improves the rejection of signal coming from off-axis targets [26].

Lastly, another way for reducing the correlation of off-axis targets is to dynamically change the way we are grouping the channels for each frame, as discussed above.

D. Display of Results

Differently than with Power Doppler signal, which is real by definition, the dot product value is a generic scalar $c = \rho e^{i\theta} \in \mathbb{C}$. The phase of this number can also be important, where we are interested in positive real values of cross correlation. Therefore, when displaying the cross correlation magnitude I, we can penalize values with a phase far away from zero as follows $$I = \rho\left(\frac{\pi - |\theta|}{\pi}\right) \quad (14)$$

assuming $\theta \in (-\pi, \pi)$. In a general aspect, the phase components of the correlation (e.g. cross-correlation) signal may be attenuated as a function of the phase value $\theta$. More particularly, the degree of attenuation may be increased for increased magnitude of the phase value, e.g. the real part. In another general aspect, the correlation signal may be attenuated as a function of the phase value.

Lastly, it is possible to normalize the correlation or cross-correlation value obtained, with respect to the product of the powers of the two signals $p_1[n]$ and $p_2[n]$, giving the normalized cross correlation or normalized cross product. This normalized value expresses the confidence in the fact that such pixel generates a signal $s[n]$ and, by consequence, that it is a pixel of a vessel; therefore such a display mode is most indicated when only information about the vessel morphology is required.

Wall Filtering

The wall filter, as previously described, is applied to every pixel and every aperture. From the cross correlation theorem, we know that the cross-correlation signal $\gamma_{xy}(\tau)$, between $x(t)$ and $y(t)$, is equal to $$\gamma_{xy}(\tau) = F[X(f)\overline{Y(f)}],$$

where $X(f)=F[x(t)]$ and $Y(f)=F[y(t)]$. F denotes Fourier Transform. Because we are assuming that we can group RF data samples in a way that noise between different groups/apertures are uncorrelated, and also that noise and Doppler signal itself are uncorrelated, we can extend all the considerations previously made on noise rejection to filtered signals.

This means that the cross correlation between the two apertures $\gamma_{p_1 p_2}(\tau)$, after filtration, is given by $$\gamma_{p_1 p_2}(O) = \int_{-\infty}^{\infty} p_1(t)\overline{p_2(t)}dt$$
$$= \int_{-\infty}^{\infty} (S(f)H_1(f))\overline{(S(f)H_2(f))}e^{j2\pi f\tau}df \bigg|_{\tau=0}$$
$$= \int_{-\infty}^{\infty} \|S(f)\|^2 H_1(f)\overline{H_2(f)}df$$

The effective filter will have an amplitude equal to the product of the two filters amplitudes: that is the amplitude of the filter whose impulse response is the convolution of the two filters.

$$\|H_1(f)\overline{H_2(f)}\| = \|H_1(f)H_2(f)\| = |F[h_1(t)*h_2(t)]|$$

This means that we can combine the filtering of different estimates in order to selectively filter different Doppler bands: as simple example, using a low pass filter on the first aperture and a high pass filter on the second one, will result in cross-correlation between frequencies around the centre the band. This allows for designing filters in which the phase can also be used to either help the estimation of the Doppler signal or to infer additional informations about the blood flow. For example, until now we have used the phase information to reject correlations with a phase far away from zero. We now describe two other possible uses of the previous relationship between the two filters and the cross correlation value.

If the two filters have the same phase spectrum, the result of the cross correlation is $$\gamma_{p_1 p_2}(0) = \int_{-\infty}^{\infty} \|S(f)\|^2 \cdot \|H_1(f)H_2(f)\|df$$

In this way, we can create a more complex filter starting from two simple ones, the simplest example being a low pass filter combined with an high pass one to enhance blood moving at a certain velocity range. Moreover, if the phases of both filters are exactly linear, it can help us to reduce correlations with a phase away from zero.

In this general case, the cross correlation is equal to $$\gamma_{p_1 p_2}(0) = \int_{-\infty}^{\infty} \|S(f)\|^2 \cdot \|H_1(f)H_2(f)\| e^{j[\theta_1(f)+\theta_2(f)]}df,$$

where $\theta_i(f)$ is the phase spectrum of the filter $H_i(f)$. In this case, we can design the phase of the filters to obtain different information about the Doppler signal. For example, if we set $H_1(z)=1+z^{-1}$ (low pass filter) and $H_2(z)=1-z^{-1}$ (high pass filter), the filter will be a band-pass filter but the integrand will have opposite sign between positive and negative frequencies, due to the zero in $z=0$ which introduces a phase shift of it at the origin.

In this case we can simplify the integral as $$\int_{-\infty}^{0} \|S(f)\|^2 \cdot \|H_1(f)H_2(f)\| e^{jk}df - \int_{0}^{\infty} \|S(f)\|^2 \cdot \|H_1(f)H_2(f)\| e^{jk}df$$

By setting $k=0$, the result will have a positive sign if the Doppler spectrum is concentrated in the positive frequency and a negative one in the opposite case. Because bandpass filtering for slow flow visualization assumes that aliasing is not significant, we can infer (as done in color Doppler) that a positive average frequency is associated with flow towards the transducer, while a negative average frequency corresponds to flow away from it. We can directly evaluate the location (positive or negative axis) of the average frequency just by looking at the sign of the cross correlation result, and therefore infer the direction of flow. Note that this is a more sensitive method than the usual Color Doppler. The reason is both because noise is suppressed, and because we are not aiming to find the velocity of blood flow but only its direction.

Material and Methods

All the acquisitions have been performed using the Verasonics data acquisition system (Verasonics, Redmond, WA), with a linear 128 elements probe with 3-12 MHz bandwidth, transmitting 4 MHz single-cycle plane waves. Both in vitro and in vivo evaluations of the method are performed.

The in-vitro experimental setup consists of a cellulose tube of 200 μm, immersed in a water tank and imaged in cross section. A solution of microbubbles, prepared as described in [27], at a concentration of 0.1 ml/L is let flow in the capillary tube using a syringe pump, with a flow rate of 375 μl/min, corresponding to roughly 20 cm/s of average velocity in the elevation direction. The scanning sequence consists of pulse inversion plane wave transmissions imaged with 7 compounded angles in the ±20 degrees range. The scanning depth is 25 mm and the tube is located roughly 15 mm below the centre of the transducer.

The in-vivo data are a rabbit kidney scan, collected with a bolus injection of SonoVue® (Bracco Spa, Milan, Italy) contrast agent, imaged using 11 compounding angles and pulse inversion, at the time of bolus arrival in the kidney region. The frame rate is about 750 frames per seconds.

Results

Figure 3:
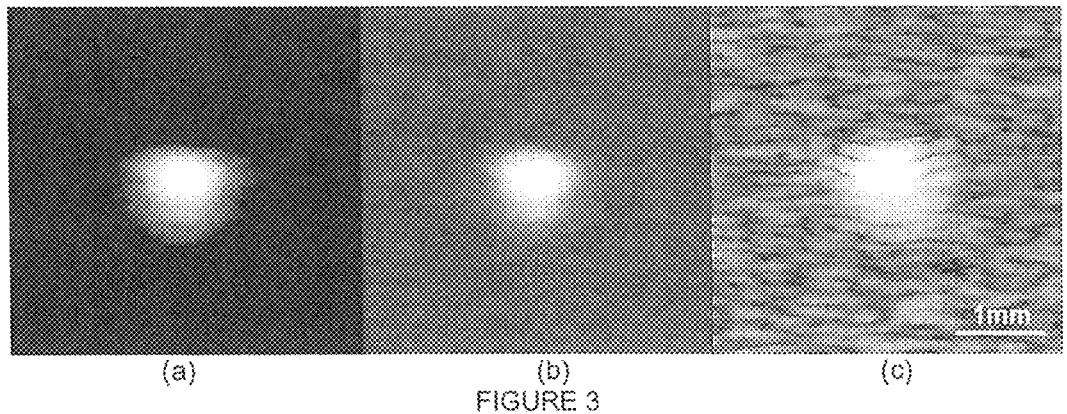
FIG. 3 shows a point spread function for (a) pulse inversion imaging, (b) Power Doppler and (c) ASAP (Acoustic Sub-Aperture Processing) for in-vitro experiments, where the depth and width axes are in mm and the dynamic range is 60 dB, normalized to the maximum of each image; the Power Doppler and ASAP images being made using 200 frames.
Figure 4:
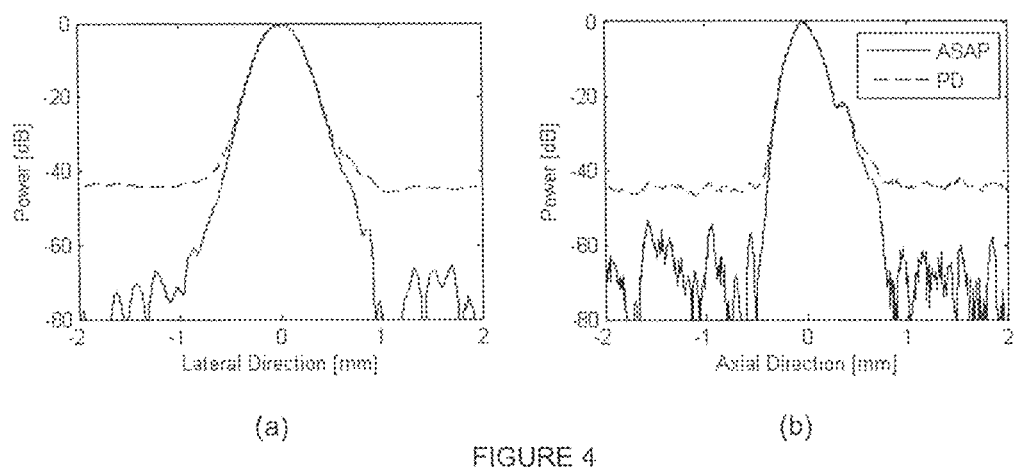
FIG. 4 shows axial (FIG. 4(a)) and lateral (FIG. 4(b)) resolution of microtube point spread functions for Power Doppler and ASAP. Spatial dimensions are in millimetres and signal power is in dB.

For the experiments in vitro, a basic Power Doppler processing is performed together with ASAP, with the channels are split over two apertures in the same way as depicted in FIG. 2(b). The point spread function (PSF) obtained in each of those cases is shown in FIG. 3. We can notice a greater noise rejection when ASAP is used instead of PD. To better evaluate this and the effects on resolution, the axial and lateral profile of such PSFs is shown in FIG. 4. It is clear that there's no noticeable difference in the resolution, while there's a substantial reduction of the noise floor, with the SNR changing from 35 dB to almost 60 dB, an improvement of 25 dB.

Figure 5:
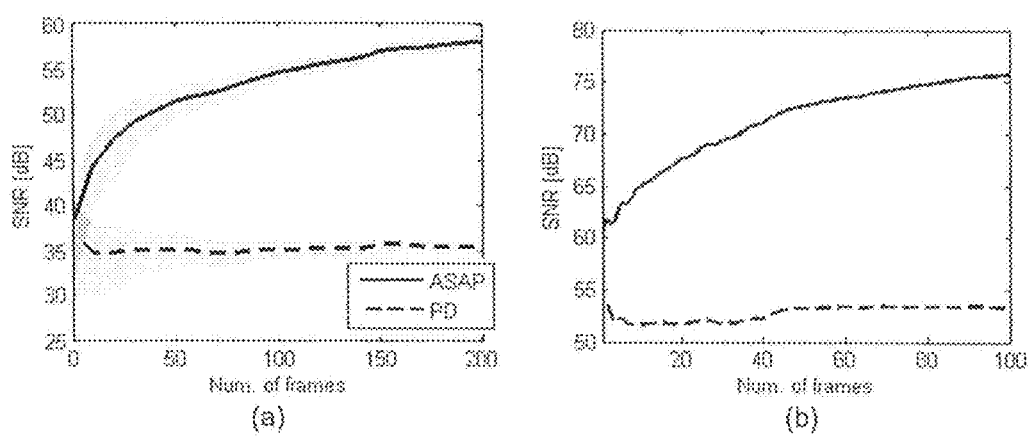
FIG. 5 shows signal to noise ratio as a function of number of frames for in vitro (FIG. 5a) and in vivo (FIG. 5b) data comparing power Doppler and ASAP processing, where in vitro results are obtained over 200 acquisitions (frames)

The ability of ASAP to improve the signal to noise ratio as more frames are acquired, is explicitly depicted in FIG. 5(a), where the SNR is plotted against number of frames. FIG. 5(a) illustrates the improvement in signal to noise ratio for ASAP with two groups (upper trace) compared against power Doppler processing (lower trace), as a function of the number of frames M used for each group of beamformed response signals, for in-vitro results. As expected, we see that Power Doppler cannot improve its estimation and the SNR is stable around 36 dB. On the other hand, already with 15 processed frames, the SNR using ASAP is about 10 dB higher than PD, and such value increases with the number of frames, reaching about 23 dB of gain when 200 frames are processed.

To understand how this technique relates to Power Doppler, we may find what is the expected value of the classical Power Doppler estimation. If we assume that the attenuation is the same for all the samples (usually a good approximation for the channels within the receive apodization window), this means that the matrix A=1 is a matrix made all of ones. With this approximation, the classical way of extracting Power Doppler signal PD[n], as used in [23], can be described similarly as eq. (12) as follows (dropping the slow time variable)

$$PD = E[\|p\|^2] = E[\|w^T(as+e)\|^2] \quad (15)$$
$$= E[(w^T as + w^T e)(\overline{w^T as + w^T e})],$$

but both w and a are vector of ones, therefore one gets $$PD = E[(N_c s + w^T e)(N_c \bar{s} + w^T \bar{e})] \quad (16)$$
$$= E[N_c^2 \|s\|^2] + E\left[\sum_{i=1}^{N_c} \|e_i\|^2\right] = N_c^2 \sigma_s^2 + N_c \sigma_c^2$$

which obviously states that, as the signal and noise are uncorrelated, the power Doppler signal made is the sum of the powers of both desired signal and noise. Note that this also shows that the noise power contributes to the power Doppler signal regardless of the integration window size.

On the other hand, if we look back at eq. (12), we get $$c(p_1, p_2) = E[w_1^T(A\sigma_s^2)w_2] = \left(\frac{N_c}{2}\sigma_s\right)^2 \quad (17)$$

meaning that our method estimates the actual true Doppler signal, rejecting any power contribution given by noise which is uncorrelated between channels (such as electronic noise).

Figure 6:
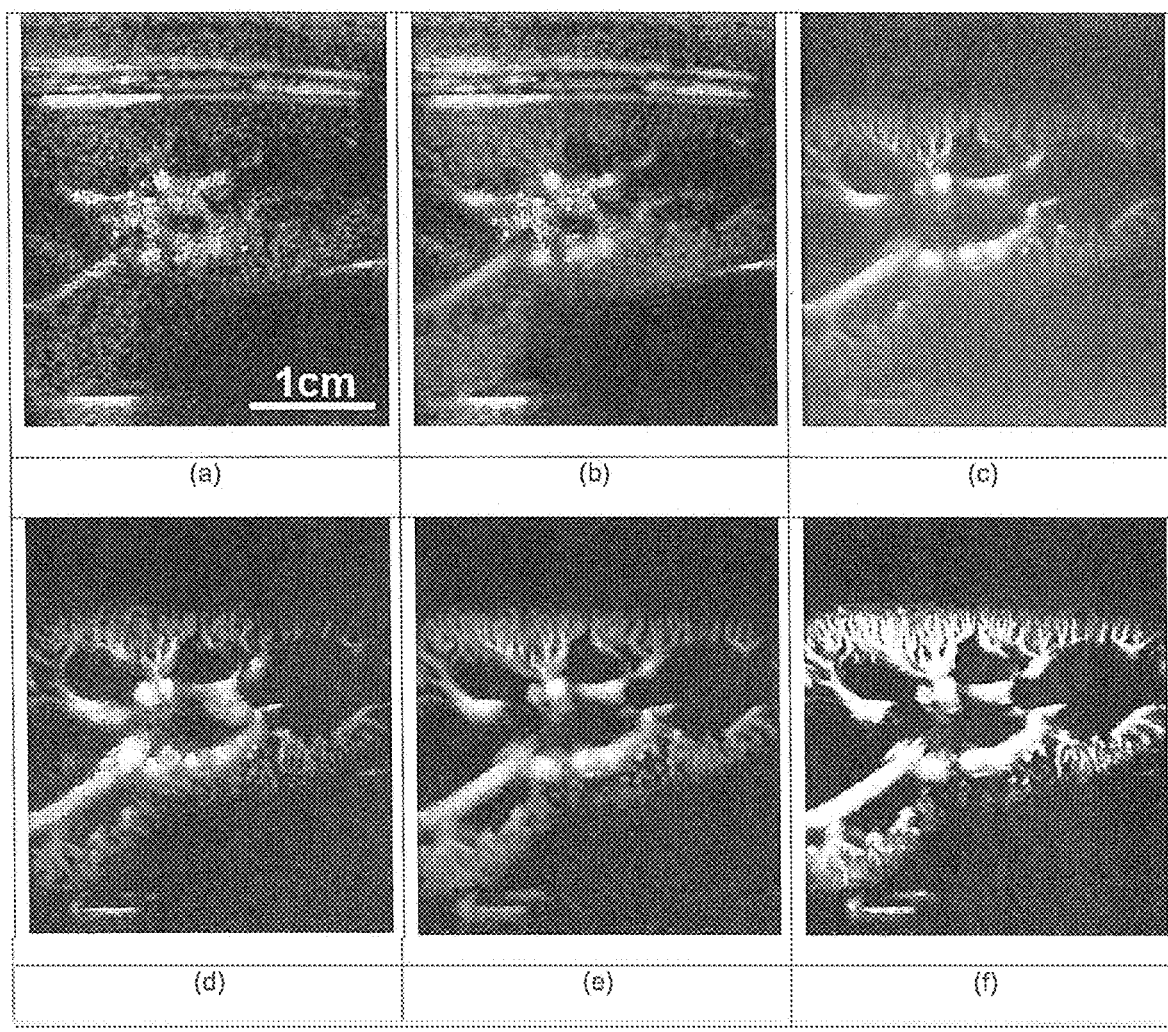
FIG. 6 shows in vivo results for image processing on a rabbit kidney after bolus injection: (a) Pulse Inversion frame, (b) averaging of 100 frames after envelope detection, (c) Power Doppler, (d) ASAP processing by grouping RF samples as in FIG. 2A(c), (e) ASAP processing by grouping RF samples as in FIG. 2A(b), and (f) shows the normalized ASAP processing of (e). All images have a dynamic range of 90 dB, except for (a) and (b) which have a dynamic range of 45 dB.

FIG. 6 illustrates two-dimensional images generated from in-vivo acquisition on a rabbit kidney after bolus injection. They depict: (a) classical Pulse Inversion frame, (b) incoherent averaging of 100 frames after envelope detection, (c) Power Doppler estimation, (d) ASAP processing by grouping RF samples as in FIG. 2B(a) (or 2A(c)), (e) ASAP processing by grouping RF samples as in FIG. 2B(b) (or 2A(b)), and (f) shows the normalized ASAP processing of (e). All images have a dynamic range of 90 dB, except for (a) and (b) which have a dynamic range of 45 dB.

Figure 9:
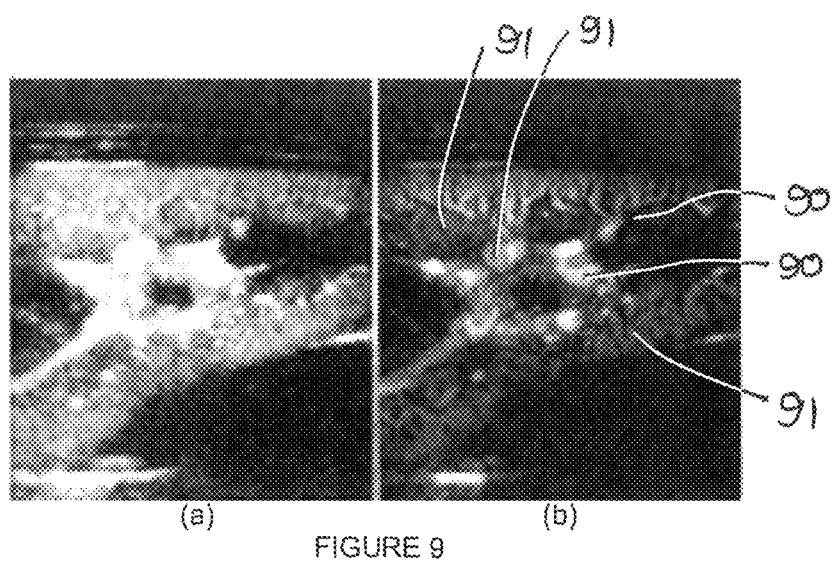

FIG. 9 illustrates images also generated from the same kidney acquisition, keeping the grouping as in FIG. 2A(b) or FIG. 2B(b).

The image in FIG. 9(a) represents flow information at a specific flow velocity range, in this case slow flow/perfusion of the kidney, through the use of different filters for the two groups. In this case, two 5th-order FIR high pass and low pass filters have been used respectively for the first and second group. Both of the filters have a quasi-linear phase spectrum. The combined result, as explained in the "Wall Filtering" section above, is a band-pass filter which highlights blood moving at slower velocities than what has been shown in the previous images, as the acoustic signal emitted by these regions is associated to a lower Doppler frequency.

FIGS. 9(b) and 9(c) represent a flow direction colour coded vascular image, as the result of applying a high pass filter, with impulse response [1, −1], to the first group and a low pass filter, impulse response [1, 1], to the second one. In this case, the zero in f=0 for the first filter causes a change of sign between the phase of positive and negative frequencies. As explained in the "Wall Filtering" section, this encodes the velocity direction in the sign of the final correlation result. As indicated by FIG. 9(b), flow towards the transducer can be colour coded in one colour (such as red, showing in the greyscale image as lighter areas 90), while flow away from the transducer can be color-coded in another colour (such as blue, showing in the greyscale image as darker areas 91). The use of colour coding is similar to existing clinical colour Doppler, but the spatial resolution and the contrast of the vessels in this case are much superior. FIG. 9(c) is an enlarged and enhanced version of FIG. 9(b) with flow towards the transducer colour coded in reds and yellows, showing in the greyscale image as lighter areas 90), while flow away from the transducer is colour coded in blue colours showing in the greyscale image as darker areas 91.

Figure 10A:
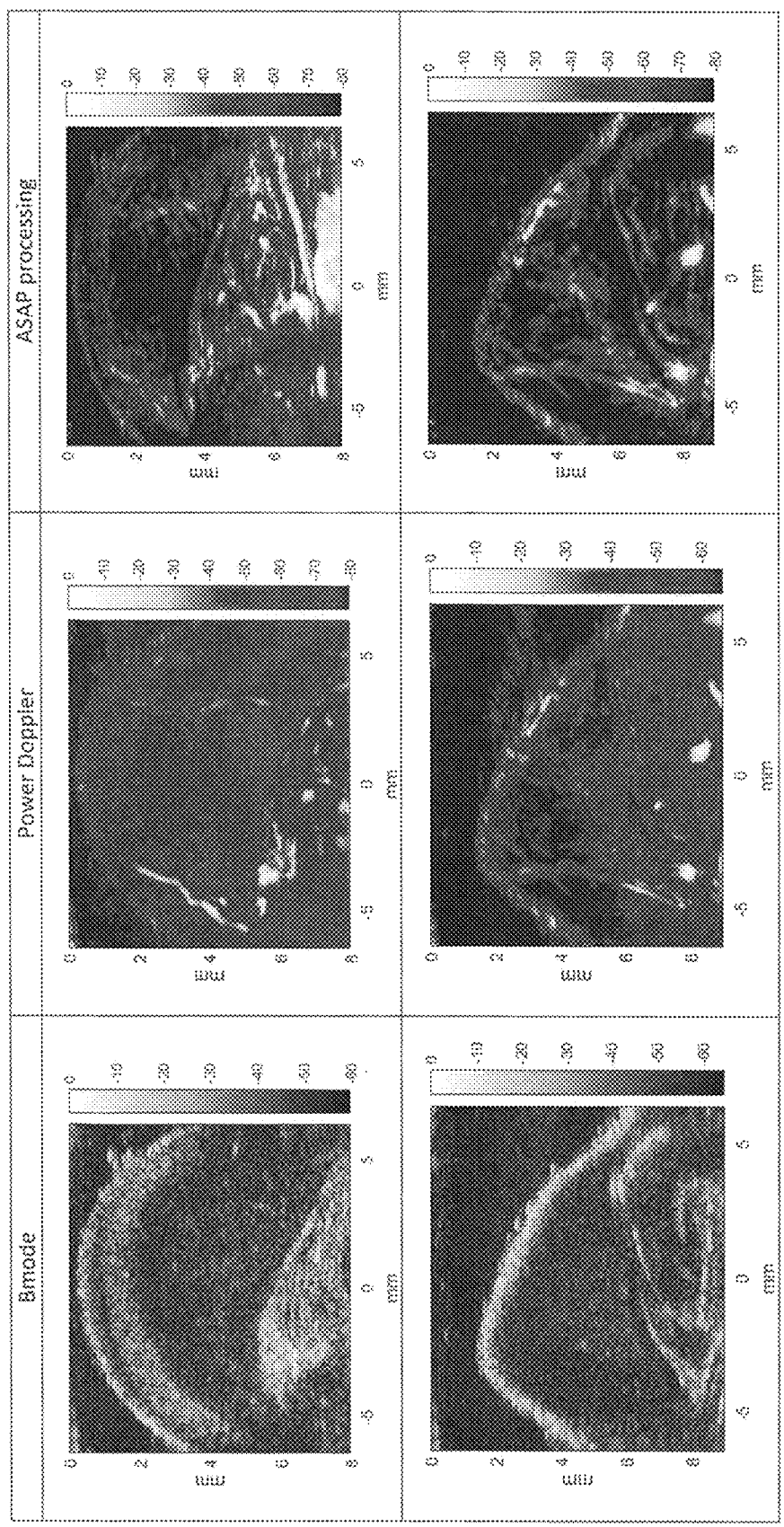
FIGS. 10A and 10B show in vivo results for image processing on a mouse tumour model after bolus injection using B-mode frame, Power Doppler, and ASAP processing by grouping RF samples as in FIG. 2A(b)
Figure 10B:
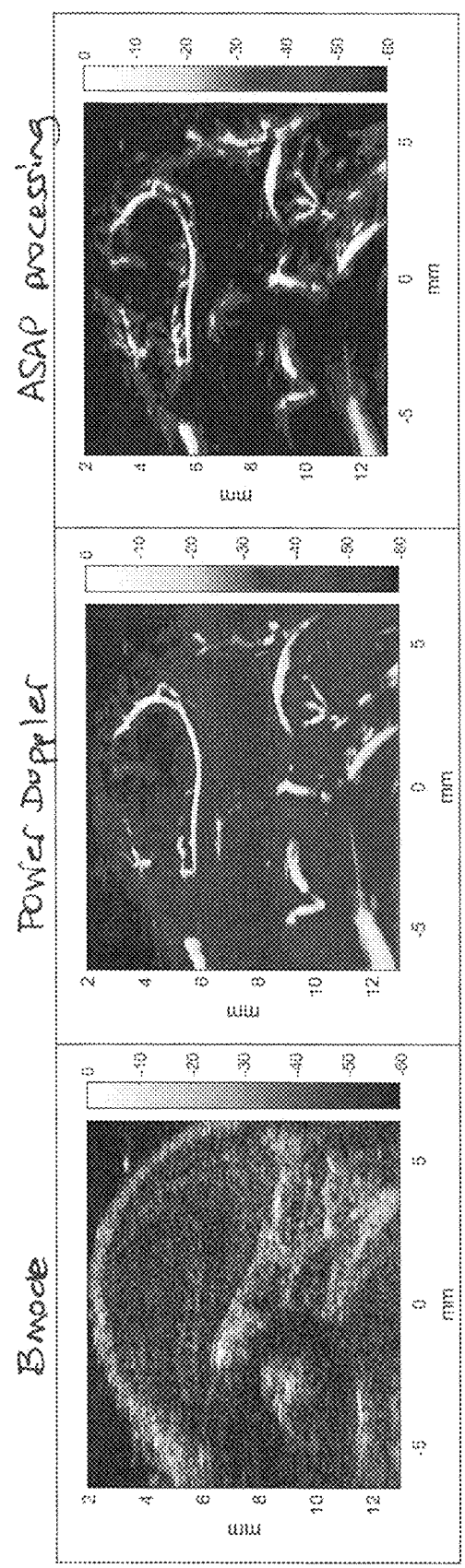

FIGS. 10A and 10B show in vivo results for image processing on a mouse tumour model after bolus injection. FIG. 10B shows a Bmode image of a tumour in a mouse model, an ultrafast power Doppler image showing tumour vasculature with noise in deep tissue, with data acquired over ~1 second Power Doppler, and an ASAP processed image using the same data set as the power Doppler, but with noise/artefact removed by grouping RF samples as in FIG. 2A(b).

Figure 7:
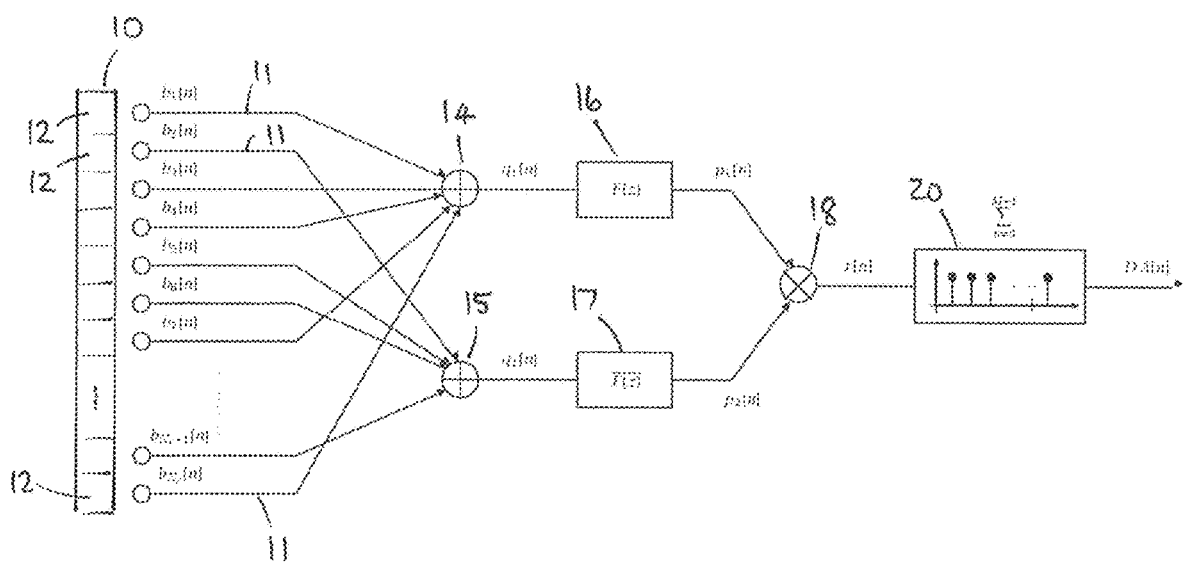
FIG. 7 shows a schematic diagram of a signal processing chain suitable for implementing the ASAP technique

FIG. 7 illustrates an exemplary signal processing chain to implement the ASAP technique in the case where the samples are grouped by channel, i.e. the channels are grouped such as illustrated in the schematic of FIG. 2A(b) or FIG. 2B(b). Each element 12 of an ultrasound transducer array 10 of N, elements produces a respective output signal $b_1[n] \ldots b_{N_c}[n]$, where n represents the output for the nth data frame. Each response signal may correspond to a channel 11, i.e. normally each element has a dedicated channel. However, multiple physical elements 12 of a transducer array 10 could be assigned to each channel 11, but the downstream processing is described in terms of the number of separate data channels available, whether each derived from a single transducer element, or multiple elements. The channels 1 . . . Nc are each divided into two groups and the response signals of the channels of the first group are coupled to a first group summation unit 14 and the response signals of the channels of the second group are coupled to a second group summation unit 15. The summation units 14, 15 perform the beamforming process, e.g. by a delay and sum process. For simplicity, the delay stages to provide spatial selection of the pixels in the field of view are not shown but are well understood in the art. Each output signal b[n] corresponds to one pixel element; outputs are generated for each pixel in fast time, and for each frame in slow time.

A first filter module 16 filters the beamformed (e.g. summed) signals of the channels of the first group and a second filter module 17 filters the beamformed (e.g. summed) signals of the channels of the second group. Exemplary filter types have been discussed above. The filtered pixel data $p_1[n]$ and $p_2[n]$ respectively from each beamformed channel are correlated in the correlation module 18 to generate a correlation output r[n]. The correlation module may be realised by a simple multiplicative junction. Estimation over M frames may be carried out with a filtering module 20, as in equation (13). The processing may be carried out in hard-wired logic or in software, or a combination of both.

In the example shown, the channel grouping is selected as channels 1, 3, 4, 7 ... Nc from group 1 and channels 2, 5, 6, ... Nc–1 for group 2. Different grouping arrangements may be selected as discussed above, and a general principle of group selection can be any selection of channels into groups which minimises the similarity of the received acoustic field outside the main lobe. In other words, it is preferable to have different sidelobes between apertures which are to be cross-correlated, to reduce the effects of off-axis targets on the signal to noise ratio. Preferably the number of physically adjacent ultrasound elements, or the number of adjacent samples, allocated to the same group is kept to a maximum unless the element spacing is large. In other words, it may be preferable that a majority of adjacent elements or samples are allocated to the same group. On the other hand, the number of adjacent samples used in the same group can't be arbitrarily large, otherwise the signal from each group will differ too much because of attenuation, apodization, angle sensitivity of transducer elements etc. A balance between the two criteria is preferable.

Figure 8:
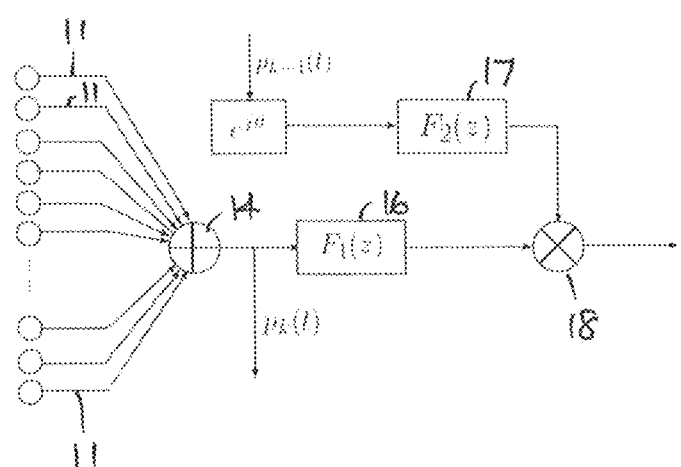
FIG. 8 shows a schematic diagram of an alternative signal processing chain suitable for implementing the ASAP technique.

FIG. 8 illustrates an exemplary signal processing chain for a possible implementation of the ASAP technique when the samples are grouped by time point, such as illustrated in the schematic of FIG. 2A(c) or FIG. 2B(a). In this example, the image is beamformed by using all the channels. Each channel 11 from a respective transducer element is coupled to a summation unit 14 for beamforming. The vertical distance between pixels is set to be equal to half the fundamental wavelength (for non-contrast acquisitions) or half the second harmonic wavelength (if contrast agent is used).

The signal from the first group of FIG. 2A(c) is denoted as p k (t) in FIG. 8. Because the vertical distance is equal to half wavelength, the signal from the second group of FIG. 2a(c) is simply given by the pixel above the current one, denoted as $p_{k-1}(t)$. The latter signal is phase shifted by the required amount. A first filter module 16 filters the beamformed (e.g. summed) signals of the samples of the first group, and a second filter module 17 filters the beamformed (e.g. summed) signals of the samples of the second group. Exemplary filter types have been discussed above. The filtered pixel data respectively from each group are correlated in correlation module 18 to generate the correlation output, similar to that described in connection with FIG. 7. With this setup, the process reduces to correlating over frames the values of pixels which are neighbours in the vertical direction.

Computational Complexity

The ASAP techniques described can be compared in complexity with classical Power Doppler to show that real time processing is feasible. Both classical PD and ASAP can be implemented in parallel processes with respect to spatial position in an image, so that each pixel can be computed independently of the others. This means that the whole process can be efficiently implemented with parallel computing devices, such as GPUs. It also means that the complexity of each pixel estimation is all we need to understand how computationally heavy the algorithm will be. The ASAP technique can be implemented with the same or similar computational load to power Doppler processing. The illustration assumes Delay and Sum as the beamforming strategy for both techniques, but other ways can be used to beamform each aperture which will lead to similar comparison results.

Delay: The same delay operation is used in both methods. If linear interpolation is employed, then this leads to $4N_c$ sums and $N_c$ products for each pixel, with $N_c$ number of channels in the receive aperture.

Sum: for PD a total of $N_c-1$ sums are required, while for ASAP N–K sums are needed, with K equal to the number of groups used.

Filter: Using the proposed [1 –1] filter, the complexity for PD is of 1 sum (and 1 sign inversion, that is a bit complement, which we consider negligible). For ASAP, this filtering is repeated at each sub-aperture, therefore we get K sums.

Power and Xcorr: whether we are finding the signal power for PD or the cross-correlation in ASAP we will perform multiplications. In PD, we multiply the output with itself, requiring one product. For ASAP, we multiply every combination of apertures and sum them together, giving a total of $$\binom{K}{2}$$

products and $$\binom{K}{2}-1$$

sums.

Temporal average: this is a FIR filter in common of both methods, which can be efficiently implemented as two sums and a buffer.

By summing all the contributions, we see that $5N_c+2$ sums are required by both methods, while $4N_c+1$ and $$4Nc+\binom{K}{2}$$

products are required by PD and ASAP respectively. As we can see, since the number of groups is usually very small, the complexity is practically similar to PD. Moreover, when only two apertures are used the complexity is the same, justifying the claim of real time application.

The filtering doesn't remove electronic noise, but it is highly advisable to have it to compensate for several other clutter signals. It can be also stated that, if no relevant motion is present, the method can be used in conjunction with low power transmissions (which minimize second harmonic generation) and microbubbles without any filtering at all.

Figure 11:
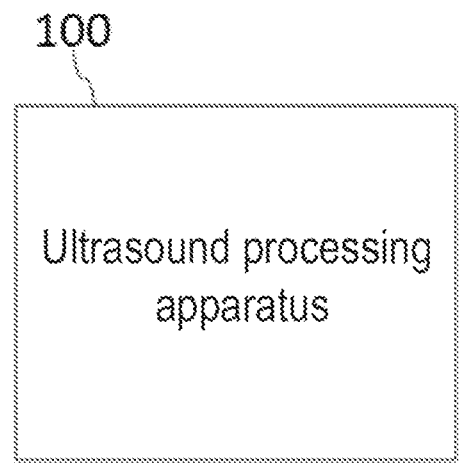
FIG. 11 shows in schematic form an ultrasound processing apparatus.

FIG. 11 shows in schematic form an ultrasound processing apparatus 100 configured to carry out the process of any of the methods described herein.

Other embodiments are intentionally within the scope of the accompanying claims.

REFERENCES

[1] D. Cosgrove, "Ultrasound contrast agents: An overview," European Journal of Radiology, vol. 60, no. 3, pp. 324-330, 2006.

[2] A. Stanziola, M. Toulemonde, Y. O. Yildiz, R. J. Eckersley, and M.-X. Tang, "Ultrasound Imaging with Microbubbles [Life Sciences]," IEEE Signal Processing Magazine, vol. 33, no. 2, pp. 111-117, 3 2016. [Online]. Available: http://ieeexplore.ieee.org/lpdocs/epic03/wrapper.htm?arnumber=7426573

[3] D. H. Simpson, C. T. Chin, and P. N. Burns, "Pulse Inversion Doppler: A New Method for Detecting Nonlinear Echoes from Microbubble Contrast Agents," vol. 46, no. 2, pp. 372-382, 1999.

[4] Y. O. Yildiz, R. J. Eckersley, R. Senior, A. K. Lim, D. Cosgrove, and M.-X. Tang, "Correction of Non-Linear Propagation Artifact in Contrast-Enhanced Ultrasound Imaging of Carotid Arteries: Methods and inVitro Evaluation," Ultrasound in Medicine & Biology, vol. 41, no. 7, pp. 1938-1947, 2015. [Online]. Available: http://linkinghub.elsevier.com/retrieve/pii/S0301562915002276

[5] F. Lin, C. Cachard, R. Mori, F. Varray, F. Guidi, and O. Basset, "Ultrasound contrast imaging: Influence of scatterer motion in multipulse techniques," IEEE Transactions on Ultrasonics, Ferroelectrics, and Frequency Control, vol. 60, no. 10, pp. 2065-2078, 2013.

[6] L. S. Wilson, "Description of Broad-Band Pulsed Doppler Ultrasound Processing Using Two-Dimensional Fourier Transform," Processing, vol. 315, pp. 301-315, 1991.

[7] G. Montaldo, M. Tanter, J. Bercoff, N. Benech, and M. Fink, "Coherent plane-wave compounding for very high frame rate ultrasonography and transient elastography," Ultrasonics, Ferroelectrics, and Frequency Control, IEEE Transactions on, vol. 56, no. 3, pp. 489-506, 2009. [Online]. Available: http://ieeexplore.ieee.org/xpl/articleDetails.jsp?arnumber=4816058

[8] E. Mace, G. Montaldo, B. F. Osmanski, I. Cohen, M. Fink, and M. Tanter, "Functional ultrasound imaging of the brain: Theory and basic principles," IEEE Transactions on Ultrasonics, Ferroelectrics, and Frequency Control, vol. 60, no. 3, pp. 492-506, 2013.

[9] J. Bercoff, G. Montaldo, T. Loupas, D. Savery, F. Meziere, M. Fink, and M. Tanter, "Ultrafast compound Doppler imaging: providing full blood flow characterization." IEEE transactions on ultrasonics, ferroelectrics, and frequency control, vol. 58, no. 1, pp. 134-47, 2011. [Online]. Available: http://www.ncbi.nlm.nih.gov/pubmed/21244981

[10] C. Errico, B. F. Osmanski, S. Pezet, O. Couture, Z. Lenkei, and M. Tanter, "Transcranial functional ultrasound imaging of the brain using microbubble-enhanced ultrasensitive Doppler," NeuroImage, vol. 124, pp. 752-761, 2016. [Online]. Available: http://dx.doi.org/10.1016/j.neuroimage.2015.09.037

[11] B.-F. Osmanski, M. Pernot, G. Montaldo, A. Bel, E. Messas, and M. Tanter, "Ultrafast Doppler imaging of blood flow dynamics in the myocardium." IEEE transactions on medical imaging, vol. 31, no. 8, pp. 1661-8, 2012. [Online]. Available: http://www.ncbi.nlm.nih.gov/pubmed/22717520

[12] C. Demene, T. Deffieux, M. Pernot, B.-F. Osmanski, V. Biran, S. Franqui, J.-M. Correas, I. Cohen, O. Baud, and M. Tanter, "Spatiotemporal clutter filtering of ultrafast ultrasound data highly increases Doppler and fUltrasound sensitivity." IEEE transactions on medical imaging, vol. PP, no. 99, p. 1, 2015. [Online]. Available: http://www.ncbi.nlm.nih.gov/pubmed/25955583

[13] Y. L. Li and J. J. Dahl, "Small-diameter Vasculature Detection with Coherent Flow Power Doppler Imaging," pp. 1-4, 2015.

[14] M. A. Lediju, G. E. Trahey, M. Jakovljevic, B. C. Byram, and J. J. Dahl, "Short-lag spatial coherence imaging," Proceedings—IEEE Ultrasonics Symposium, pp. 987-990, 2010.

[15] M. A. Lediju, G. E. Trahey, B. C. Byram, and J. J. Dahl, "Shortlag spatial coherence of backscattered echoes: Imaging characteristics," IEEE Transactions on Ultrasonics, Ferroelectrics, and Frequency Control, vol. 58, no. 7, pp. 1377-1388, 2011.

[16] E. Bullitt, D. Zeng, G. Gerig, S. Aylward, S. Joshi, J. K. Smith, W. Lin, and M. G. Ewend, "Vessel tortuosity and brain tumor malignancy: A blinded study1," Academic Radiology, vol. 12, no. 10, pp. 1232-1240, 2005. [Online]. Available: http://www.sciencedirect.com/science/article/pii/S1076633205005647

[17] P. Carmeliet et al., "Angiogenesis in health and disease," Nature medicine, vol. 9, no. 6, pp. 653-660, 2003.

[18] R. C. Gessner, C. B. Frederick, F. S. Foster, and P. A. Dayton, "Acoustic angiography: a new imaging modality for assessing microvasculature architecture," Journal of Biomedical Imaging, vol. 2013, p. 14, 2013.

[19] K. K. Shung, Diagnostic ultrasound: Imaging and blood flow measurements. CRC press, 2015.

[20] C. Demené, M. Pernot, V. Biran, M. Alison, M. Fink, O. Baud, and M. Tanter, "Ultrafast doppler reveals the mapping of cerebral vascular resistivity in neonates," Journal of Cerebral Blood Flow & Metabolism, vol. 34, no. 6, pp. 1009-1017, 2014.

[21] J. Bercoff, G. Montaldo, T. Loupas, D. Savery, F. Mézière, M. Fink, and M. Tanter, "Ultrafast compound doppler imaging: providing full blood flow characterization," Ultrasonics, Ferroelectrics, and Frequency Control, IEEE Transactions on, vol. 58, no. 1, pp. 134-147, 2011.

[22] B.-F. Osmanski, M. Pernot, G. Montaldo, A. Bel, E. Messas, and M. Tanter, "Ultrafast doppler imaging of blood flow dynamics in the myocardium," Medical Imaging, IEEE Transactions on, vol. 31, no. 8, pp. 1661-1668, 2012.

[23] E. Macé, G. Montaldo, I. Cohen, M. Baulac, M. Fink, and M. Tanter, "Functional ultrasound imaging of the brain," Nature Methods, vol. 8, no. 8, pp. 662-664, 2011.

[24] A. Bar-Zion, C. Tremblay-Darveau, O. Solomon, D. Adam, and Y. C. Eldar, "Super-Resolution Ultrasound Imaging of Vascular Structures with High Temporal Resolution," ArXiv e-prints, January 2016.

[25] C. H. Seo and J. T. Yen, "Sidelobe suppression in ultrasound imaging using dual apodization with cross-correlation," IEEE Transactions on Ultrasonics, Ferroelectrics, and Frequency Control, vol. 55, no. 10, pp. 2198-2210, 2008.

[26] J. Shin, Y. Chen, M. Nguyen, and J. T. Yen, "Robust ultrasonic reverberation clutter suppression using Multi-Apodization with Crosscorrelation," IEEE International Ultrasonics Symposium, IUS, pp. 543-546, 2014.

[27] C. H. Leow, E. Bazigou, R. J. Eckersley, A. C. H. Yu, P. D. Weinberg, and M.-X. Tang, "Flow Velocity Mapping Using Contrast Enhanced High-Frame-Rate Plane Wave Ultrasound and Image Tracking: Methods and Initial in Vitro and in Vivo Evaluation." Ultrasound in medicine & biology, vol. 41, no. 11, pp. 2913-2925, 2015.

[28] Synnevag, J. F., Andreas Austeng, and Sverre Holm. "Minimum variance adaptive beamforming applied to medical ultrasound imaging." *Proc. IEEE Ultrason. Symp.* Vol. 2. No. 3. 2005.

The invention claimed is:

1. A method for ultrasound data processing comprising:
   i) transmitting ultrasound excitation signals from elements of a transducer array;
   ii) receiving response signals from elements of the transducer array, each response signal corresponding to a respective channel;
   iii) sampling each response signal at one or more time points in the response signal to create a plurality of samples, each sample corresponding to a channel and a time point;
   iv) dividing the plurality of samples into at least two different or partially overlapping groups;
   v) beamforming the response signals from the first group;
   vi) beamforming the response signals from the second group;
   vii) repeating steps i) to vi) for M data frames, wherein a data frame comprises sampled response signals in respect of each of a plurality of pixels of an image space for a given ultrasound transmission and where M is greater than 1;
   viii) multiplying pixelwise the beamformed signals of each group and averaging the multiplication over the M data frames, resulting in improved signal-to-noise ratio and comprising:
      generating, for each data frame of the M data frames, a sample output, wherein the sample output comprises an integral over the M data frames or the M data frames-temporal frequency of the beamformed response signals from the first group multiplied by the beamformed response signals from the second group for that data frame, wherein the beamformed response signals from the first or second group is conjugate transformed before integration, and
      averaging the sample output for a first data frame with the sample outputs from subsequent data frames up to the $M^{th}$ data frame; and
   ix) providing the averaged sample outputs as an image output for at least a first pixel of the plurality of pixels of the image space.

2. The method of claim 1 in which the first group comprises samples from the same time point of each of a plurality of channels and the second group comprises samples from that same time point of each of a different plurality of channels.

3. The method of claim 1 in which the first group comprises samples from a first time point of each of a plurality of channels and the second group comprises samples from a second time point of each of the same plurality of channels.

4. The method of claim 1 in which the first group comprises samples from a first time point of each of a first plurality of channels and a second time point of each of a second plurality of channels, and the second group comprises samples from the first time point of each of the second plurality of channels and the second time point of each of the first plurality of channels.

5. The method of claim 1 in which the at least two groups of samples are selected according to at least one of the following conditions:
   each sample is allocated to only one group;
   each group has the same number of samples;
   a majority of adjacent elements in the array are allocated to different groups;
   a majority of the data samples are not common in the different groups,
   samples are allocated to the groups randomly or adaptively by optimizing a measure of the received data.

6. The method of claim 1 further including filtering each beamformed set of response signals to suppress clutter signal components or other unwanted components.

7. The method of claim 6 in which filtering each beamformed set of response signals comprises filtering with a high pass filter.

8. The method of claim 7 in which the high pass filter is one of a derivative estimator; a second order FIR filter and an IIR filter.

9. The method of claim 1 in which step viii) comprises attenuating the multiplied beamformed signals as a function of the phase value of the multiplied beamformed signals.

10. The method of claim 1 in which step viii) produces a final sample output and further comprises applying different filters for each group of response signals so as to include the phase of a Doppler spectrum in the final sample output, to infer blood dynamics information or using phase components of the multiplied beamformed signals to infer blood dynamics information.

11. The method of claim 10 in which the blood dynamics information comprises direction of flow.

12. The method of claim 1 further including normalizing the sample outputs with respect to the magnitude of the beamformed response signals.

13. The method of claim 6 in which step viii) comprises using different filters for each group, thereby obtaining a more complex filtering and/or include phase information in the multiplication to select different flow velocities.

14. The method of claim 13 in which the different filters are designed with a phase shift between positive and negative frequencies, in order to extract flow direction information.

15. The method of claim 1 further including displaying a magnitude of the averaged sample outputs for each of the plurality of pixels in a two dimensional array of pixels of image space, in a process of ultrasound imaging.

16. The method of claim 1 in which the process is carried out substantially in real time with the collection of response signals in respect of each of the plurality of pixels of image space and for a succession of the M data frames.

17. An ultrasound processing apparatus configured to:
   i) transmit ultrasound excitation signals from elements of a transducer array;
   ii) receive response signals from elements of the transducer array, each response signal corresponding to a respective channel;
   iii) sample each response signal at one or more time points in the response signal to create a plurality of samples, each sample corresponding to a channel and a time point;
   iv) divide the plurality of samples into at least two different or partially overlapping groups;
   v) beamform the response signals from the first group;
   vi) beamform the response signals from the second group;
   vii) repeat steps i) to vi) for M data frames, wherein a data frame comprises sampled response signals in respect of each of a plurality of pixels of an image space fora given ultrasound transmission and where M is greater than 1;

viii) multiply pixelwise the beamformed signals of each group and average the multiplication over the M data frames, resulting in improved signal-to-noise ratio and comprising:

generating, for each data frame of the M data frames, a sample output, wherein the sample output comprises an integral over the M data frames or the M data frames-temporal frequency of the beamformed response signals from the first group multiplied by the beamformed response signals from the second group for that data frame, wherein the beamformed response signals from the first or second group is conjugate transformed before integration, and averaging the sample output for a first data frame with the sample outputs from subsequent data frames up to the Mth data frame; and ix) provide the averaged sample outputs as an image output for at least a first pixel of the plurality of pixels of the image space.

\* \* \* \* \*